(12) United States Patent
Wang et al.

(10) Patent No.: US 7,169,743 B2
(45) Date of Patent: Jan. 30, 2007

(54) STABILIZED THICKENED HYDROGEN PEROXIDE CONTAINING COMPOSITIONS WITH A MIXTURE OF STABILIZERS

(75) Inventors: Xue Wang, King of Prussia, PA (US); Keith Genco, Millersville, PA (US); Claire Jaubert, King of Prussia, PA (US); Benoit Requieme, Charly (FR)

(73) Assignee: Arkema Inc., Philadelphia, PA (US)

( * ) Notice: Subject to any disclaimer, the term of this patent is extended or adjusted under 35 U.S.C. 154(b) by 0 days.

(21) Appl. No.: 11/267,764

(22) Filed: Nov. 4, 2005

(65) Prior Publication Data

US 2006/0063695 A1 Mar. 23, 2006

Related U.S. Application Data

(63) Continuation of application No. 11/023,705, filed on Dec. 28, 2004, now Pat. No. 7,045,493.

(60) Provisional application No. 60/586,682, filed on Jul. 9, 2004.

(51) Int. Cl.
C11D 3/395 (2006.01)
C11D 3/37 (2006.01)

(52) U.S. Cl. ............... 510/375; 510/302; 510/309; 510/367; 510/372; 510/434; 510/253; 510/318

(58) Field of Classification Search ............. 510/375, 510/302, 309, 367, 372, 434, 253, 318
See application file for complete search history.

(56) References Cited

U.S. PATENT DOCUMENTS

| | | | |
|---|---|---|---|
| 2,158,525 A | 5/1939 | Riedl et al. | |
| 2,624,655 A | 1/1953 | Greenspan | |
| 2,782,100 A | 2/1957 | Greenspan | |
| 3,122,417 A | 2/1964 | Bruno Blaser et al. | |
| 3,383,174 A | 5/1968 | Carnnie et al. | |
| 3,387,939 A | 6/1968 | Reilly | |
| 3,681,022 A | 8/1972 | Kibbel | |
| 3,781,409 A | 12/1973 | Munday et al. | |
| 3,929,678 A | 12/1975 | Laughlin et al. | |
| 4,061,721 A | 12/1977 | Strong | |
| 4,070,442 A | 1/1978 | Watts | |
| 4,294,575 A | 10/1981 | Kowalski | |
| 4,304,762 A | 12/1981 | Leigh | |
| 4,525,291 A | 6/1985 | Smith | |
| 4,552,668 A | 11/1985 | Brown | |
| 4,552,675 A | 11/1985 | Brown | |
| 4,684,517 A | 8/1987 | Clipper et al. | |
| 4,702,857 A | 10/1987 | Gooselink | |
| 4,927,627 A * | 5/1990 | Schrader et al. | ............... 424/62 |
| 4,981,662 A | 1/1991 | Dougherty | |
| 5,078,672 A | 1/1992 | Dougherty et al. | |
| 5,102,575 A | 4/1992 | Lanniel | |
| 5,130,053 A | 7/1992 | Feasey et al. | |
| 5,169,552 A | 12/1992 | Wise | |
| 5,217,710 A | 6/1993 | Williams | |
| 5,302,311 A | 4/1994 | Sugihara et al. | |
| 5,372,802 A | 12/1994 | Barrows | |
| 5,550,009 A | 8/1996 | Haye et al. | |
| 5,733,474 A | 3/1998 | Kagermeier | |
| 5,736,497 A * | 4/1998 | Steiner | ............... 510/303 |
| 5,817,253 A * | 10/1998 | Grimberg et al. | ...... 252/186.29 |
| 5,997,764 A | 12/1999 | Ambuter | |
| 6,083,422 A | 7/2000 | Ambuter | |
| 6,495,501 B1 | 12/2002 | Del Duca | |
| 6,536,628 B2 | 3/2003 | Montgomery | |
| 6,576,213 B1 | 6/2003 | Falgen et al. | |
| 7,045,493 B2 * | 5/2006 | Wang et al. | ............... 510/375 |
| 2002/0114757 A1 | 8/2002 | Tenney | |
| 2003/0073150 A1 | 4/2003 | Woerner | |

FOREIGN PATENT DOCUMENTS

| | | |
|---|---|---|
| EP | 376 704 A1 | 7/1990 |
| EP | 0426949 A1 | 5/1991 |
| GB | 909895 | 11/1962 |
| JP | 62114979 | 11/1985 |
| JP | 04349109 A | 12/1992 |
| WO | WO 9109807 A2 | 7/1991 |
| WO | WO 92/19287 A1 | 11/1992 |
| WO | WO 93/22273 A1 | 11/1993 |
| WO | WO 96/09983 | 4/1996 |
| WO | WO 96/12003 A1 | 4/1996 |
| WO | WO 97/11676 | 4/1997 |
| WO | WO 99/18180 A1 | 4/1999 |
| WO | WO 00/76916 A1 | 12/2000 |

* cited by examiner

Primary Examiner—Charles Boyer
(74) Attorney, Agent, or Firm—Steven D. Boyd

(57) ABSTRACT

Stabilized thickened hydrogen peroxide containing compositions are disclosed. The compositions contain a stabilizer system made up of a stannate stabilizer, a phosphorus containing stabilizer or a mixture of phosphorus containing stabilizers; and an aromatic chelating agent or a mixture of aromatic chelating agents. The compositions are suitable for use as disinfectants, as cleaning agents, and in various personal care applications such as hair care and tooth whitening.

24 Claims, No Drawings

STABILIZED THICKENED HYDROGEN PEROXIDE CONTAINING COMPOSITIONS WITH A MIXTURE OF STABILIZERS

CROSS-REFERENCE TO RELATED APPLICATIONS

This application is a continuation of U.S. patent application Ser. No. 11/023,705, filed Dec. 28, 2004 now U.S. Pat. No. 7,045,493 which claims priority on U.S. Provisional Application Ser. No. 60/586,682, filed Jul. 9, 2004, incorporated herein by reference.

FIELD OF THE INVENTION

This invention relates to stabilization of hydrogen peroxide containing compositions. In particular, this invention relates stabilized thickened hydrogen peroxide containing compositions suitable for use in a variety of disinfectant, cleaning, personal care, pharmaceutical, textile, and industrial applications.

BACKGROUND OF THE INVENTION

To avoid the disadvantages inherent in the use of hypochlorite solutions in cleaning compositions, manufacturers of these products have developed alternative compositions based on aqueous hydrogen peroxide. Hydrogen peroxide is generally acceptable from a toxicological and environmental standpoint because its decomposition products are oxygen and water. In addition, these compositions are also fiber-safe and color-safe.

Polymeric thickening agents are added to cleaning compositions to increase their residence time on non-horizontal surfaces as well as to enhance the aesthetics of the composition, to provide ease of use, and to suspend other components of the composition. Decomposition of hydrogen peroxide caused by catalytically active substances, such as metal ions, is extremely difficult to prevent. In addition, many of conventional polymeric thickening agents accelerate the decomposition of hydrogen peroxide and are themselves unstable in the presence of hydrogen peroxide. Thus, it has been extremely difficult to produce compositions that have the required stability. With excessive decomposition of the hydrogen peroxide, the composition loses its cleaning ability. In addition, decomposition of the polymeric thickening agent reduces the viscosity of the cleaning composition, reducing its ability to cling to non-horizontal surfaces.

Consequently, stabilizers have been developed to improve the stability of thickened hydrogen peroxide containing compositions. Stabilizers are discussed, for example, in Ambuter, U.S. Pat. Nos. 5,997,764, and 6,083,422, the disclosures of which are incorporated herein by reference. Although these stabilizers increase the shelf life of thickened hydrogen peroxide containing compositions, none of these stabilizers is totally satisfactory. Thus, a need exists for thickened hydrogen peroxide containing compositions with increased stability.

SUMMARY OF THE INVENTION

The invention is a thickened hydrogen peroxide containing composition. The composition comprises:
a) about 0.5 wt % to about 15 wt % of hydrogen peroxide;
b) water;
c) about 0.05 wt % to 10 wt % of a polymeric thickening agent or a mixture of polymeric thickening agents;
d) a stabilizer system comprising:
   i) about 10 ppm to about 1% of a stannate stabilizer;
   ii) about 10 ppm to about 1% of a phosphorus containing stabilizer or a mixture of phosphorus containing stabilizers; and
   iii) about 10 ppm to about 1% of an aromatic chelating agent or a mixture of aromatic chelating agents; and
in which the composition has a viscosity of greater than about 500 cP.

Thickened hydrogen peroxide containing compositions that comprise the three component stabilizer system are storage stable.

DETAILED DESCRIPTION OF THE INVENTION

Unless otherwise indicated, the terms phosphonic acid chelating agent, aromatic chelating agent, stannate stabilizer, surfactant, polymeric thickening agent, pyrophosphate, aqueous base, and similar terms also include mixtures of such materials. Unless otherwise specified, all percentages are percentages by weight (wt %), and all temperatures are in degrees Centigrade (Celsius).

The invention is a stabilized thickened hydrogen peroxide containing composition. It comprises hydrogen peroxide, water, a polymeric thickening agent, and a stabilizer system made up of three components: a phosphorus containing stabilizer or mixture of phosphorus containing stabilizers, a stannate stabilizer, and an aromatic chelating agent or mixture of aromatic chelating agents. If the stabilized thickened hydrogen peroxide containing composition is to be used as a cleaning composition, other ingredients that are conventional components of cleaning compositions, such as a surfactant or a mixture of surfactants, are present.

Polymeric Thickening Agent

The stabilized thickened hydrogen peroxide containing composition comprises a polymeric thickening agent or a mixture of polymeric thickening agents, which helps control dispensing of the composition, retards drainage from non-horizontal surfaces to which the composition is applied, and helps suspend other components of the composition. Although the concentration of the polymeric thickening agent or agents will depend on the viscosity desired for the final composition, the nature of the polymeric thickening agent or agents present, and the nature and concentration of other materials present in the composition, the stabilized thickened hydrogen peroxide containing composition typically comprises about 0.01 to about 10 wt %, preferably 0.05 to about 5 wt %, more preferably about 0.05 to about 2.5 wt %, and still more preferably about 0.25 to about 2.0 wt % of the polymeric thickening agent, or if more than one polymeric thickening agent is present, agents. The polymeric thickening agents can be dispersed in water and neutralized with base to thicken the hydrogen peroxide containing composition and form a gel.

Polymeric thickening agents include, for example, synthetic polymers, cellulose esters, and biopolymers. Synthetic polymers include, for example, homopolymers and copolymers of olefinically unsaturated carboxylic acid and/or anhydride monomers, such as acrylic acid, methacrylic acid, maleic anhydride, itaconic anhydride, etc. A preferred carboxylic acid is acrylic acid. The copolymers are preferably copolymers of a carboxylic acid monomer and a hydrophobic monomer. Typically hydrophobic monomers include long chain carbon chain acrylate or methacrylate esters such as decyl acrylate, lauryl acrylate, stearyl acrylate, behenyl acrylate, and the corresponding methacrylate esters, and aromatic monomers, such as styrene and substituted styrenes. These polymers typically have molecular weights of about 10,000 to about 900,000 or more. The polymers may also be crosslinked. Other useful polymeric thickening agents are disclosed in Ambuter, U.S. Pat. No. 5,997,764, column 6, line 1, to column 7, line 29, the disclosure of which is incorporated herein by reference.

Cellulose esters include, for example, carboxymethyl cellulose, methyl cellulose, ethyl cellulose, hydroxypropyl cellulose, hydroxypropyl methyl cellulose, etc. Biopolymers include, for example, xanthan gum, locust bean gum, guar gum, carob bean gum, konjac, carrageenans, alginates, pectin, etc. Xanthan gum, for example, is a high molecular weight polysaccharide produced by the microorganism *Xanthomonas campestris*.

The viscosity of the thickened hydrogen peroxide composition will depend on the polymeric thickening agent or agents used in the composition, their concentration, and the viscosity desired for the intended use of the composition. Polyacrylate thickening agents typically provide a viscosity of about 10,000 to 100,000 cP. Xanthan gum thickening agent typically provides a viscosity of about 500 cP to about 1,500 cP. Tooth whitening gels typically have a viscosity of greater than about 10,000 cP. Liquid detergents, which must be pourable, typically have a viscosity of about 500 cP to about 2,000 cP.

Stabilizer System

The stabilized thickened hydrogen peroxide containing compositions comprise a three component stabilizer system. The stabilizer system comprises: (a) about 10 ppm to about 1 wt %, preferably about 15 ppm to about 2500 ppm (0.25 wt %), more preferably about 20 ppm to about 1000 ppm (0.1 wt %), even more preferably about 50 ppm to about 500 ppm, of a stannate stabilizer; (b) about ppm to about 1 wt %, preferably about 15 ppm to about 2500 ppm (0.25 wt %), more preferably about 20 ppm to about 1000 ppm (0.1 wt %), even more preferably about 40 ppm to about 500 ppm, of a phosphorus containing stabilizer or, if more than one phosphorus containing stabilizer is used, of a mixture of phosphorus containing stabilizers; and (c) about 10 ppm to about 1 wt %, preferably about ppm to about 2500 ppm (0.25 wt %), more preferably about 20 ppm about to 1000 ppm (0.1 wt %), even more preferably about 30 ppm to about 600 ppm, of an aromatic chelating agent or, if more than one aromatic chelating agent is used, of a mixture of aromatic chelating agents. In one embodiment, the stabilizer system comprises about 30 ppm to about 500 ppm, typically 60 ppm to 300 ppm, of each of three components. Typically, the upper limit for the amount of each component and for the system as a whole will be determined by economics and by the degree of stabilization required.

As will be apparent to those skilled in the art, in certain pH ranges one or more of these stabilizer components may be present as its corresponding anion or anions, or as an equilibrium mixture of the component and its corresponding anion or anions. Anions of these stabilizer components and mixtures of these stabilizer components and their corresponding anion or anions are included in the definition of each of these stabilizer components and are within the scope of the claims.

Phosphorus containing stabilizers include pyrophosphates (such as, for example, $Na_4P_2O_7$, $Na_3HP_2O_7$, $Na_2H_2P_2O_7$, and $K_2H_2P_2O_7$) and phosphonic acid chelating agents. Phosphonic acid chelating agents include, for example, compounds of the general structure $N(CR^1R^2PO_3H_2)_3$, in which $R^1$ and $R^2$ are each independently hydrogen or an alkyl group of one to four carbon atoms, such as amino tri (methylene phosphonic acid) (ATMP) (DEQUEST® 2000, Solutia, St. Louis, Mo., USA), in which $R^1$ and $R^2$ are each hydrogen; diethylene triamine penta(methylene phosphonic acid) (DTPA) (DEQUEST® 2066); hexamethylene diamine tetra(methylene phosphonic acid) (DEQUEST® 2054); bis hexamethylene triamine penta methylene phosphonic acid (DEQUEST®) 2090); and compounds of the general structure $C(R^3)(PO_3H_2)_2OH$, in which $R^3$ is hydrogen or an alkyl group of one to four carbon atoms, such as 1-hydroxyethylidene-1,1-diphosphonic acid (HEDP) (DEQUEST® 2010) ($C(CH_3)(PO_3H_2)_2OH$). Preferred phosphorus-based chelating agents include 1-hydroxyethylidene-1,1-diphosphonic acid, amino tri(methylene phosphonic acid), and diethylene triamine penta(methylene phosphonic acid).

The stannate stabilizer may be formed in situ from hydrolysis of a tin compound, such as tin sulfate, sodium stannate ($Na_2SnO_3.3(H_2O)$), tin dichloride, or tin tetrachloride. Although the stannate stabilizer is believed to be colloidal stannic oxide, it is typically referred to as colloidal sodium stannate or sodium stannate.

The thickened hydrogen peroxide containing composition comprises an aromatic chelating agent or a mixture of aromatic chelating agents. While not being bound by any theory of explanation, it is believed that this compound functions as a radical scavenger. The aromatic structure includes carbocyclic aromatic rings, such as the benzene or naphthalene ring, as well as heteroaromatic rings such as pyridine and quinoline. The stabilizer should also contain chelating groups, such as hydroxyl, carboxyl, phosphonate, or sulfonate.

The aromatic chelating agent may be, for example, salicylic acid; a substituted salicylic acid, such as 3-methylsalicylic acid, 4-methyl salicylic acid, 5-methyl salicylic acid, 6-methyl salicylic acid, 3,5-dimethyl salicylic acid, 3-ethyl salicylic acid, 3-iso-propyl salicylic acid, 3-methoxy salicylic acid, 4-methoxy salicylic acid, 5-methyoxy salicylic acid, 6-methoxy salicylic acid, 4-ethoxy salicylic acid, 5-ethyoxy salicylic acid, 2-chloro salicylic acid, 3-chloro salicylic acid, 4-chloro salicylic acid, 5-choloro salicylic acid, 3,5-dichloro salicylic acid, 4-fluoro salicylic acid, 5-fluoro salicylic acid, 6-fluoro salicylic acid; or a mixture thereof. The aromatic chelating agent may be, for example, 8-hydroxy-quinoline; a substituted 8-hydroxy-quinoline, such as, 5-methyl-8-hydroxy-quinoline, 5-methoxy-8-hydroxy-quinoline, 5-chloro-8-hydroxy-quinoline, 5,7-dichloro-8-hydroxy-quinoline, 8-hydroxy-quinoline-5-sulfonic acid, or a mixture thereof. The aromatic chelating agent may be, for example, a pyridine-2-carboxylic acid, such as picolinic acid (2-pyridinecarboxylic aid); dipicolinic acid (2,6-pyridinedicarbxylic acid); 6-hydroxy-picolinic acid; a substituted 6-hydroxy-picolinic acid, such as 3-methyl-6-hydroxy-picolinic acid, 3-methoxy-6-hydroxy-picolinic acid, 3-chloro-6-hydroxy-picolinic acid, 3,5-dichloro-6-hydroxy-picolinic acid; or a mixture thereof. Preferred aromatic chelating agents include, salicylic acid, 6-hydroxy-picolinic acid, and 8-hydroxy-quinoline.

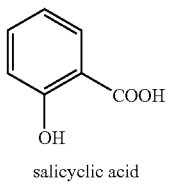
salicyclic acid

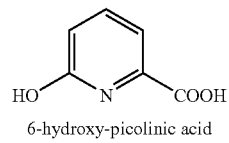
6-hydroxy-picolinic acid

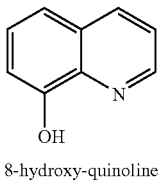
8-hydroxy-quinoline

Other Ingredients

The stabilized thickened hydrogen peroxide containing composition can be used as, for example, a disinfectant lotion or in the oxidative dying of hair. However, if the stabilized thickened hydrogen peroxide containing composition is to be used a cleaning composition, it may comprise other components that are conventional ingredients of cleaning compositions.

The composition may also comprise a surfactant or a mixture of surfactants. Numerous surfactants useful in cleaning compositions are well known. Surfactants are well known to those skilled in the art and are described, for example, in *McCutcheon's Detergents and Emulsifiers*, Manufacturing Confectioners Publishing Company, Glen Rock, N.J., and in *Encyclopedia of Surfactants*, Volumes I–III, Compiled by M. and I. Ash, Chemical Publishing Co., NY. Surfactants useful in cleaning compositions are disclosed in, for example, Wise, U.S. Pat. No. 5,169,552; Gosselink, U.S. Pat. No. 4,702,857, especially column 17, line 27, to column 22, line 19, and Laughlin, U.S. Pat. No. 3,929,678, especially column 5, line 65, to column 36, line 30. The concentration of the surfactant or the mixture of surfactants is typically about 0.25 wt % to about 25 wt %, more typically about 1.0 wt % to 15 wt %, of the composition. Preferably the surfactant or surfactants do not contain functional groups that are susceptible to oxidation by the hydrogen peroxide, such as carbon carbon double bonds, hydroxyl groups, etc.

Nonionic surfactants are typically condensation products of a hydrophobic organic aliphatic compound, such as a long chain aliphatic alcohol, and hydrophilic ethylene oxide and/or propylene oxide. The length of the resulting polyether chain can be adjusted to achieve the desired balance between the hydrophobic and hydrophilic properties. Nonionic surfactants include, for example, ethoxylated and propoxylated alcohols, especially $C_{8-20}$ alcohols, with 2 to 100 moles of ethylene oxide and/or propylene oxide per mole of alcohol, especially ethoxylates of primary alcohols containing about 8 to 18 carbon atoms in a straight or branched chain configuration with about 5 to 30 moles of ethylene oxide, for example, the ethoxylates of decyl alcohol, cetyl alcohol, lauryl alcohol, or myristyl alcohol; ethoxylates of secondary aliphatic alcohols containing 8 to 18 carbon atoms in a straight or branched chain configuration with 5 to 30 moles of ethylene oxide; condensation of aliphatic alcohols containing about 8 to abut 20 carbon atoms with ethylene oxide and propylene oxide; polyethylene glycol and polyethylene oxide; ethoxylated hydrogenated castor oil; and ethoxylates of sorbitan esters.

Anionic surfactants include, for example, alkyl ether phosphates, alkyl aryl sulphonates, alkyl ether sulphates, alkyl sulphates, aryl sulphonates, carboxylated alcohol ethoxylates, olefin sulphonates, succinates, fatty acid soaps, alkyl diphenyl disulfonates, etc., and mixtures thereof. Examples of anionic surfactants are: sodium cetyl sulfate, sodium lauryl sulfate (SLS), sodium myristyl sulfate, and sodium stearyl sulfate, sodium dodecylbenzene sulfonate, and sodium polyoxyethylene lauryl ether sulfate.

Other conventional ingredients may be included, provided each ingredient is compatible with the other ingredients of the thickened hydrogen peroxide containing composition and the presence of the ingredient does not adversely affect the properties of the thickened hydrogen peroxide containing composition. Each additional ingredient is used to modify the thickened hydrogen peroxide containing composition in conventional form and is present in an effective amount, that is, in the amount required to achieve the desired effect without adversely affecting the properties of the composition.

The stabilized thickened hydrogen peroxide containing compositions used in, for example, cleaning applications, may also comprise a perfumes and fragrances, typically at about 0.03 to about 0.5 wt % of the composition. Fluorescent whitening agents may also be present, typically at about 0.1 to 1.0 wt %. An anti-redeposition agent, such as, polyvinyl pyrrolidone, hydroxyethyl cellulose, sodium carboxymethyl cellulose, and hydroxypropyl ethyl cellulose may be present. A filler salt, such as sodium sulfate or sodium chloride, may be present. Other conventional ingredients include: dyes and other colorants; fabric softening compositions; static control agents; optical opacifiers, such as polystyrene particles; and suds regulants, such as dimethylpolysiloxane.

The stabilizer system may be used over a wide pH range. However, the pH of the stabilized thickened hydrogen peroxide containing composition may be less than about 9, typically less than about 8, more typically about 3 to about 7, even more typically about 5 to about 7. Although a buffer, such as a phosphate buffer, may be included to maintain pH at the desired value, this may not be necessary in all cases.

Hydrogen Peroxide

The stabilized thickened hydrogen peroxide containing composition typically comprises about 0.5 wt % to about 15 wt %, typically about 1 wt % to about 10 wt %, more typically about 2 wt % to about 8 wt %, even more typically about 3 wt % to about 5 wt %, of hydrogen peroxide. Hydrogen peroxide ($H_2O_2$) is commercially available, and its preparation has been described in numerous patents and publication. The anthraquinone process (also called the autoxidation process or the Riedl-Pfleiderer process) is described, for example, in Riedl, U.S. Pat. No. 2,158,525, and in the *Kirk-Othmer Encyclopedia of Chemical Technology*, 3rd. ed., Volume 13, Wiley, New York, 1981, pp. 15–22.

It may be necessary to add base, such as aqueous sodium hydroxide or aqueous potassium hydroxide, to the composition until the desired pH is attained. Aqueous sodium hydroxide is preferred. The base should be free from metal ions that would catalyze decomposition of hydrogen peroxide, such as ferrous ions, ferric ions, cupric ions, cuprous ions, manganous ions, and similar transition metal ions. The base should also be free from both organic and inorganic materials that would react with the hydrogen peroxide.

After all the other ingredients have been accounted for, water comprises the balance of the thickened hydrogen peroxide containing composition. Because hydrogen peroxide is typically commercially available as a 30 wt % to 70 wt % aqueous solution, it is typically necessary to dilute the hydrogen peroxide with water to obtain the desired hydrogen peroxide concentration. The water should be free from metal ions that would catalyze decomposition of hydrogen peroxide, such as ferrous ions, ferric ions, cupric ions, cuprous ions, manganous ions, and similar transition metal ions. The water should also be free from organic material that would be oxidized by hydrogen peroxide. The water should also be free of inorganic materials that would react with hydrogen peroxide, such as chlorine ($Cl_2$), hypochorous acid (HOCl), and sodium hypochlorite (NaOCl). Distilled or deionized water is preferred.

INDUSTRIAL APPLICABILITY

The stabilized thickened hydrogen peroxide containing compositions may be used in a variety of disinfectant, cleaning, personal care, pharmaceutical, textile and industrial applications. They disinfect the surfaces into which they are brought into contact and so can be used as disinfectant solutions or disinfectant lotions. When a surfactant is present, they both clean and disinfect the surfaces into which they are brought into contact. They can be applied by any method that insures good contact between the object to be cleaned and/or disinfected and the composition, such as spraying or wiping, and then removed by, for example, rinsing with water and/or wiping. The stabilized thickened hydrogen peroxide containing compositions may also be used, for example, as liquid detergents and in oral care applications, such as in tooth bleaching compositions.

They can also be used in oxidative dying, which is extensively used for the dying of hair. In the oxidative dying process, hydrogen peroxide is used in combination with one or more oxidative hair coloring agents, generally small molecules capable of diffusing into hair and comprising one or more primary intermediates and one or more couplers. The hydrogen peroxide activates the small molecules of primary intermediates so that they react with couplers to form larger sized compounds in the hair shaft to color the hair in a variety of shades and colors. Typical primary intermediates include p-phenylenediamine, p-toluenediamine, p-aminophenol, and 4-amino-3-methylphenol. Typical couplers include resorcinol, 2-methylresorcinol, 3-aminophenol, and 5-amino-2-methylphenol. The color depends on the primary intermediate(s) and coupler(s) used. Typically, the hydrogen peroxide is a 3 wt % to 12 wt %, preferably a 6 wt %, aqueous solution, which can be a viscous liquid or gel. In general, the hair dyeing composition comprising the primary intermediate(s) and coupler(s) is prepared and then, at the time of use, mixed with the stabilized thickened hydrogen peroxide containing composition until an essentially homogenous composition is obtained. Shortly after its preparation, the resulting composition is applied to the hair to be dyed and permitted to remain in contact with the hair for about 2 to about 60 min, typically about 15 to 45 min, especially about 30 min, at about 15 to 50° C. The hair is rinsed with water, and dried. If necessary, it is washed with a shampoo and rinsed, e.g., with water or a weakly acidic solution, such as a citric acid or tartaric acid solution. Subsequently the hair is dried.

The advantageous properties of this invention can be observed by reference to the following examples, which illustrate but do not limit the invention.

EXAMPLES

Glossary

ACULYN® 28 Acrylates/Beheneth-25 Methacrylate Copolymer (Rohm and Haas, Philadelphia, Pa., USA)
CARBOPOL® 2020 Polyacrylate polymeric thickening agent (Noveon, Cleveland, Ohio, USA)
CARBOPOL® EZ-2 Polyacrylate polymeric thickening agent (Noveon, Cleveland, Ohio, USA)
CARBOPOL® EZ-3 Polyacrylate polymeric thickening agent (Noveon, Cleveland, Ohio, USA)
DTPA Diethylene triamine penta(methylene phosphonic acid) (DEQUEST® 2066) (Solutia, St. Louis, Mo., USA)
HEDP 1-Hydroxyethylidene-1,1-diphosphonic acid (DEQUEST® 2010) (Solutia, St. Louis, Mo., USA)
RHODOPOL® T Xanthum gum polymeric thickening agent (Rhodia, Cranbury, N.J., USA)
Sodium Stannate Sodium stannate, $Na_2SnO_3.3H_2O$
Pyrophosphate $Na_2H_2P_2O_7$

General Procedures

Preparation Stabilized 50% Hydrogen Peroxide Solutions

Stabilizers were mixed with deionized water to make a standard stabilizer system solution. The 50% stabilized hydrogen peroxide solution was prepared by adding the stabilizer system to 70% hydrogen peroxide, and diluting the resulting stabilized hydrogen peroxide to 50% hydrogen peroxide with deionized water.

Preparation of Thickened Hydrogen Peroxide Containing Compositions

Except where indicated, the samples contain 5–6% hydrogen peroxide and 0.4–3% polymeric thickening agent. The polymeric thickening agent (0.7 g) was added to 60 g of deionized water and mixed well. The stabilizers were added to the hydrogen peroxide solutions before the polymeric thickening agents. Sodium hydroxide solution (8%) was added until the mixture thickened. 50% Hydrogen peroxide (7 ml) and water were added to make 70 g of the thickened hydrogen peroxide containing composition, which was a hydrogen peroxide containing gel. The pH was adjusted to 5 to 7 with 8% aqueous sodium hydroxide. The stabilizer concentration given for each sample is the concentration of the active ingredient in the final sample.

Stability Evaluation

Unless otherwise indicated, the following procedure was followed for stability evaluation. The samples were put in a 40° C. to 50° C. oven. The viscosity of the composition and, in some cases, the concentration of hydrogen peroxide in the composition, was measured during the storage period. Viscosity, in cP, was measured with Brookfield RVTD Digital Viscometer and Brookfield KYNAR® resin coated spindle #6T. Hydrogen peroxide concentration was measured by titration with potassium permanganate.

Example 1

This example shows the change in viscosity and hydrogen peroxide concentration for samples that contain a polyacrylate polymeric thickening agent and various stabilizers. The following samples were prepared and evaluated as described in the General Procedures. The results are shown in Table 1.

Each of the samples contained 5 wt % hydrogen peroxide and 1 wt % CARBOPOL® EZ-2 polymeric thickening agent. The pH was 6. The storage temperature was 45° C.

Sample 1-A contains <1 ppm of $Na_2H_2P_2O_7$.

Sample 1-B contains 150 ppm of salicylic acid and <1 ppm of $Na_2H_2P_2O_7$.

Sample 1-C contains 150 ppm of HEDP and <1 ppm of $Na_2H_2P_2O_7$.

Sample 1-D contains 300 ppm of sodium stannate and <1 ppm of $Na_2H_2P_2O_7$.

Sample 1-E contains 300 ppm of sodium stannate, 150 ppm of HEDP, 150 ppm of salicylic acid and <1 ppm of $Na_2H_2P_2O_7$.

TABLE 1

| Examples | | Time (weeks) | | | |
|---|---|---|---|---|---|
| | | 0 | 1 | 2 | 3 |
| 1-A | Viscosity (cP) | 37,500 | 50 | ND[a] | ND |
| | $H_2O_2$ (wt %) | 4.84 | 0.76 | ND | ND |
| 1-B | Viscosity (cP) | 50,000 | 50 | ND | ND |
| | $H_2O_2$ (wt %) | 4.97 | 0.98 | ND | ND |
| 1-C | Viscosity (cP) | 50,000 | 14,000 | 50 | ND |
| | $H_2O_2$ (wt %) | 4.70 | 4.79 | 1.15 | ND |
| 1-D | Viscosity (cP) | 50,000 | 43,500 | 37,500 | 19,000 |
| | $H_2O_2$ (wt %) | 4.81 | 4.78 | 4.77 | 4.75 |
| 1-E | Viscosity (cP) | 50,000 | 42,000 | 39,000 | 36,500 |
| | $H_2O_2$ (wt %) | 4.88 | 4.76 | 4.69 | 4.55 |

[a]ND means not determined.

Sample 1-A contains almost no stabilizer, and Samples 1-B to 1-D contain only one of the stabilizers. Both the viscosity and the hydrogen peroxide concentration of these samples rapidly decreased on storage temperature at 45° C. Although the hydrogen peroxide concentration of Sample 1-D, the sodium stannate containing sample, did not decrease as rapidly as in the other samples, the viscosity of this sample decreased during the test period.

Sample 1-E contains a stabilizer system of the invention. Both viscosity and hydrogen peroxide decreased less during the test period.

Example 2

This example shows the change in viscosity for samples that contain a polyacrylate polymeric thickening agent and a stabilizer system of the invention. The following samples were prepared and evaluated as described in the General Procedures. The results are shown in Table 2.

Each of the samples contained 5 wt % hydrogen peroxide and 3 wt % ACULYN®28 polymeric thickening agent. The pH is adjusted to 6. The storage temperature is 45° C.

Sample 2-A contains less than 1 ppm $Na_2H_2P_2O_7$.

Sample 2-B contains 300 ppm sodium stannate, 150 ppm HEDP, 150 ppm salicylic acid, and less than 1 ppm $Na_2H_2P_2O_7$.

TABLE 2

| Examples | | Time (weeks) | | | | | | |
|---|---|---|---|---|---|---|---|---|
| | | 0 | 1 | 2 | 3 | 4 | 5 | 6 |
| 2-A | Viscosity (cP) | 50000 | 50 | ND | ND | ND | ND | ND |
| | $H_2O_2$ (wt %) | 4.37 | 0.43 | ND | ND | ND | ND | ND |
| 2-B | Viscosity (cP) | 50000 | 50000 | 50000 | 50000 | 50000 | 42000 | 41000 |
| | $H_2O_2$ (wt %) | 4.06 | 3.93 | 3.9 | 3.91 | 3.88 | 3.94 | 3.81 |

Sample 2-A contains almost no stabilizer. Both the viscosity and the hydrogen peroxide concentration of this sample rapidly decreased on storage temperature at 45° C.

Sample 2-B contains a stabilizer system of the invention. Both viscosity and hydrogen peroxide decreased only slightly during the six-week test period.

Example 3

This example shows the change in viscosity for samples that contain a polyacrylate polymeric thickening agent and a stabilizer system of the invention. The following samples were prepared and evaluated as described in the General Procedures. The results, showing viscosity in cP, are shown in Table 3.

Each of the samples contained 1 wt % 1% CARBOPOL® 2020 polymeric thickening agent. The pH is adjusted to 7. The storage temperature is 50° C.

Sample 3-A contained 0 wt % hydrogen peroxide.

Sample 3-B contained 5 wt % hydrogen peroxide and <1 ppm $Na_2H_2P_2O_7$.

Sample 3-C contained 5 wt % hydrogen peroxide, 40 ppm $Na_2SnO_3 \cdot 3H_2O$, 200 ppm HEDP, 500 ppm 6-hydroxyl picolinic acid, and <1 ppm $Na_2H_2P_2O_7$.

TABLE 3

| Examples[a] | Time (weeks) | | | | |
|---|---|---|---|---|---|
| | 0 | 1 | 2 | 3 | 4 |
| 3-A | 128,000 | 46,000 | 15,400 | 600 | 800 |
| 3-B | 134,200 | 800 | ND | ND | ND |
| 3-C | 112,400 | 60,600 | 41,000 | 33,600 | 28,600 |

[a]Viscosity, in cP

Sample 3-B contained less than 1 ppm of stabilizers. The viscosity reduced more than 90% within 1 week. The viscosity of sample 3-C, which contained a stabilizer system of the invention, decreased less than that of Sample 3-A, which does not contain hydrogen peroxide.

Example 4

This example shows the change in viscosity for samples that contain a polyacrylate polymeric thickening agent and a stabilizer system of the invention. The following samples were prepared and evaluated as described in the General Procedures. The results, showing viscosity in cP, are shown in Table 4.

Each of the samples contained 1 wt % CARBOPOL® EZ 3 polymeric thickening agent. The pH was adjusted to 5. The storage temperature was 50° C.

Sample 4-A contained 0% hydrogen peroxide.

Sample 4-B contained 5% hydrogen peroxide and <1 ppm $Na_2H_2P_2O_7$.

Sample 4-C contained 5% hydrogen peroxide, 80 ppm $Na_2SnO_3 \cdot 3H_2O$, 40 ppm $Na_2H_2P_2O_7$, 50 ppm of 8-hydroxy quinoline, and <1 ppm $Na_2H_2P_2O_7$.

TABLE 4

| Examples[a] | Time (week) | | | | |
|---|---|---|---|---|---|
| | 0 | 1 | 2 | 3 | 4 |
| 4-A | 180,800 | ND | 128,600 | 89,600 | 74,000 |
| 4-B | 0 | 0 | 0 | 0 | 0 |
| 4-C | 194,600 | ND | 135,200 | 98,400 | 43,800 |

[a]Viscosity, in cP

Sample 4-B, with no stabilizer, could not maintain viscosity while being prepared. During the test period, Sample 4-C, which contains a stabilizer system of the invention, was comparable in stability to Sample 4-A, which does not contain hydrogen peroxide.

Example 5

This example shows the change in viscosity for samples that contain a stabilizer system of the invention and xanthan gum as the polymeric thickening agent. Except were indicated, the following samples were prepared and evaluated as described in the General Procedures. The thickening agent was 0.4% RHODOPOL® T xanthan gum. The pH was adjusted to 5 with 85% phosphoric acid (2 ppm). The storage temperature was 40° C. Viscosities, in cP, for these samples, were measured with the Brookfield DVII Viscometer and Brookfield spindle #2. The results, showing viscosity in cP, are shown in Table 5.

Sample 5-A contained 0% hydrogen peroxide.

Sample 5-B contained 6% hydrogen peroxide, 2 ppm of $Na_2H_2P_2O_7$ and 625 ppm DEQUEST® 2066.

Sample 5-C contained 6% hydrogen peroxide with 2 ppm $Na_2H_2P_2O_7$, 625 ppm DEQUEST® 2066, and 500 ppm sodium salicylate.

Sample 5-D contained 6% hydrogen peroxide with 2 ppm $Na_2H_2P_2O_7$, 625 ppm DEQUEST® 2066, 500 ppm sodium salicylate, and 25 ppm sodium stannate.

TABLE 5

| Examples[a] | Time (days) | | | | | |
|---|---|---|---|---|---|---|
| | 0 | 6 | 7 | 14 | 21 | 24 | 28 |
| 5-A | 1105 | ND | 937 | 895 | 847 | ND | 720 |
| 5-B | 1175 | 1130 | ND | 972 | 802 | 672 | ND |
| 5-C | 1252 | ND | 1207 | 1092 | 942 | ND | 637 |
| 5-D | 1260 | ND | 1233 | 1155 | 1070 | ND | 930 |

[a]Viscosity, in cP

With a stabilizer system of the invention, sample 5-D is much more stable than Sample 5-B, which only contains phosphorus-based stabilizers and Sample 5-C, which contains phosphonate and salicylate as stabilizers. It appears to be even more stable than the sample without hydrogen peroxide (5-A).

Having described the invention, we now claim the following and their equivalents.

What is claimed is:

1. A composition comprising:
   a) about 0.5 wt % to about 15 wt % of hydrogen peroxide;
   b) water;
   c) about 0.01 wt % to 10 wt % of a polymeric thickening agent or a mixture of polymeric thickening agents; and
   d) a stabilizer system comprising;
      i) about 10 ppm to about 1% of a stannate stabilizer;
      ii) about 10 ppm to about 1% of a phosphorus containing stabilizer or a mixture of phosphorus containing stabilizers; and
      iii) about 10 ppm to about 1% of an aromatic chelating agent selected from the group consisting of 6-hydroxy-picolinic acid, substituted 6-hydroxy-picolinic acid, 8-hydroxy-quinoline, substituted 8-hydroxy-quinolines pyridine-2-carboxylic acid and mixtures thereof;
   in which the composition has a viscosity of greater than about 500 cP.

2. The composition of claim 1 in which the composition comprises about 15 ppm to about 2500 ppm of the stannate stabilizer; about 15 ppm to about 2500 ppm of the phosphorus containing stabilizer or the mixture of phosphorus containing stabilizers; and about 15 ppm to about 2500 ppm of the aromatic chelating agent or the mixture of aromatic chelating agents.

3. The composition of claim 2 in which:
   the phosphorus containing stabilizer or stabilizers are selected from the group consisting of pyrophosphate, compounds of the structure $N(CR^1R^2PO_3H_2)_3$, in which $R^1$ and $R^2$ are each independently hydrogen or an alkyl group of one to four carbon atoms, diethylene triamine penta(methylene phosphonic acid), hexamethylene diamine tetra(methylene phosphonic acid), bis hexamethylene triamine penta methylene phosphonic acid, and compounds of the general structure $C(R^3)(PO_3H_2)_2OH$, in which $R^3$ hydrogen or an alkyl group of one to four carbon atoms.

4. The composition of claim 3 in which the polymeric thickening agent or polymeric thickening agents are selected from the group consisting of homopolymers and copolymers of acrylic acid, and the composition comprises about 0.05 wt % to about 5 wt % of the polymeric thickening agent.

5. The composition of claim 4 in which the composition has a pH of about 3 to about 7.

6. The composition of claim 5 in which the composition comprises about 20 ppm to about 1000 ppm of the stannate stabilizer; about 20 ppm to about 1000 ppm of the phosphorus containing stabilizer or the mixture of phosphorus containing stabilizers; and about 20 ppm to about 1000 ppm of the aromatic chelating agent or the mixture of aromatic chelating agents.

7. The composition of claim 6 in which the composition comprises about 50 ppm to about 500 ppm of the stannate stabilizer; about 40 ppm to about 500 ppm of the phosphorus containing stabilizer or the mixture of phosphorus containing stabilizers; and about 30 ppm to about 600 ppm of the aromatic chelating agent or the mixture of aromatic chelating agents.

8. The composition of claim 7 in which the phosphorus containing stabilizer or stabilizers are selected from the group consisting of pyrophosphate, amino tri(methylene phosphonic acid), diethylene triamine penta(methylene phosphonic acid), hexamethylene diamine tetra(methylene phosphonic acid), bis hexamethylene triamine yenta methylene phosphonie acid, and 1-hydroxyethylidene-1,1-diphosphonic acid; and the aromatic chelating agent or agents are selected from the group consisting of 6-hydroxy-picolinic acid and 8-hydroxy-quinoline.

9. The composition of claim 1 in which the composition additionally comprises about 0.25 wt % to about 25 wt % of a surfactant or a mixture of surfactants.

10. The composition of claim 9 in which the composition comprises about 15 ppm to about 2500 ppm of the stannate stabilizer; about 15 ppm to about 2500 ppm of the phosphorus containing stabilizer or the mixture of phosphorus containing stabilizers; and about 15 ppm to about 2500 ppm of the aromatic chelating agent or the mixture of aromatic chelating agents.

11. The composition of claim 10 in which the composition has a pH of about 3 to about 7.

12. The composition of claim 11 in which the composition has a viscosity of about 10,000 cP to about 100,000 cP.

13. The composition of claim 12 in which the thickening agent is a polyacrylate thickening agent.

14. The composition of claim 11 in which the composition has a viscosity of about 500 cP to about 2,000 cP.

15. The composition of claim 14 in which the thickening agent is xanthan gum.

16. The composition of claim 11 in which the phosphorus containing stabilizer or stabilizers are selected from the group consisting of pyrophosphate, compounds of the structure $N(CR^1R^2PO_3H_2)_3$, in which $R^1$ and $R^2$ are each independently hydrogen or an alkyl group of one to four carbon atoms, diethylene triamine penta(methylene phosphonic acid), hexamethylene diamine tetra(methylene phosphonic acid), bis hexamethylene triamine penta methylene phosphonic acid, and compounds of the general structure $C(R^3)(PO_3H_2)_2OH$, in which $R^3$ is hydrogen or an ailcyl group of one to four carbon atoms.

17. The composition of claim 16 in which the composition comprises about 20 ppm to about 1000 ppm of the stannate stabilizer; about 20 ppm to about 1000 ppm of the phosphorus containing stabilizer or the mixture of phosphorus containing stabilizers; and about 20 ppm to about 1000 ppm of the aromatic chelating agent or the mixture of aromatic chelating agents.

18. The composition of claim 17 in which the composition comprises about 50 ppm to about 500 ppm of the stannate stabilizer; about 40 ppm to about 500 ppm of the phosphorus containing stabilizer or the mixture of phosphorus containing stabilizers; and about 30 ppm to about 600 ppm of the aromatic chelating agent or the mixture of aromatic chelating agents.

19. The composition of claim 18 in which the phosphorus containing stabilizer or stabilizers are selected from the group consisting of pyrophosphate, amino tri(methylene phosphonic acid), diethylene triamine penta(methylene phosphonic acid), hexaxmethylene diamine tetra(methylene phosphonic acid), bis hexamethylene triamine penta methylene phosphonic acid, and 1-hydroxyethylidene-1,1-diphosphonic acid; and the aromatic chelating agent or agents are selected from the group consisting of 6-hydroxy-picolinic acid and 8-hydroxy-quinoline.

20. The composition of claim 19 in which the composition comprises about 0.05 wt % to about 2.5 wt % of the polymeric thickening agent and about 2 wt % to 8 wt % of hydrogen peroxide.

21. The composition of claim 20 in which the composition has a viscosity of about 10,000 cP to about 100,000 cP.

22. The composition of claim 21 in which the thickening agent is a polyacrylate thickening agent.

23. The composition of claim 20 in which the composition has a viscosity of about 500 cP to about 2,000 cP.

24. The composition of claim 23 in which the thickening agent is xanthan gum.

* * * * *